United States Patent [19]

Hori et al.

[11] Patent Number: 4,542,215
[45] Date of Patent: Sep. 17, 1985

[54] METHOD FOR PREPARING 8-ACYLTHIO-1,2,3,4,5,6-HEXAHYDRO-2,6-METHANO-3,6(E),11(A)-TRIMETHYL-3-BENZAZOCINES

[75] Inventors: Mikio Hori, Gifu; Hajime Fujimura, Kyoto, both of Japan

[73] Assignee: Wako Pure Chemical Industries, Ltd., Osaka, Japan

[21] Appl. No.: 496,151

[22] Filed: May 19, 1983

[30] Foreign Application Priority Data

May 19, 1982 [JP] Japan .................................. 57-85183
Nov. 29, 1982 [JP] Japan .................................. 57-207616

[51] Int. Cl.[4] .................. C07D 401/12; C07D 221/26
[52] U.S. Cl. ..................................... 544/126; 544/333; 546/97
[58] Field of Search .................... 546/97; 544/126, 333

[56] References Cited

PUBLICATIONS

Jacobson, A., et al., *J. Med. Chem.*, 8(5), 563 (1965).
March, J., *Advanced Organic Chemistry*, McGraw Hill, New York, 1968, pp. 402 and 901.
*Chemical Abstracts*, 90:22526m (1979) [Demoute, J., et al., *J. Chem. Res.* (5)1978, (7), 244–5].
Shiotani, S., et al., *Chem. Pharm. Bull.* (Japan), 20(2), 277–283 (1972).
Bordwell, F., et al., *J. Am. Chem. Soc.*, 73, 2251 (1951).
Hori, M., et al., *Heterocycles*, 20(12), 2359 (1983).
Bottino, F., et al., *J. Org. Chem.*, 46(13), 2793 (1981).

*Primary Examiner*—Richard A. Schwartz
*Attorney, Agent, or Firm*—Sughrue, Mion, Zinn, Macpeak and Seas

[57] ABSTRACT

A method for preparing 8-acylthio-1,2,3,4,5,6-hexahydro-2,6-methano-3,6(e),11(a)-trimethyl-3-benzazocines represented by general formula (I) below

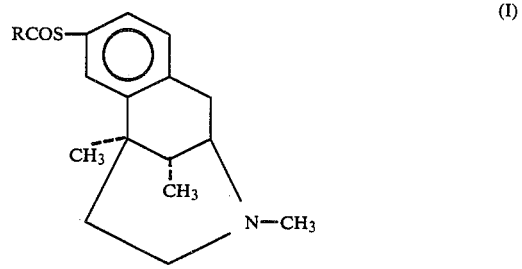

(I)

wherein R represents an alkyl group, a phenyl group or a heterocyclic group, which comprises reacting 1,2,3,4,5,6-hexahydro-2,6-methano-3,6(e),11(a)-trimethyl-3-benzazocine represented by the formula (II) below

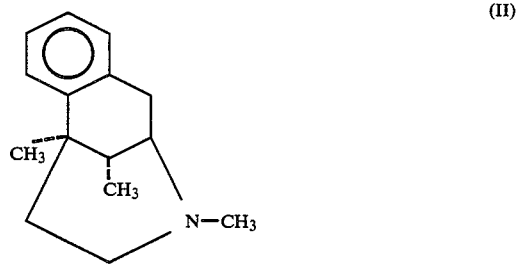

(II)

or its salt with chlorosulfonic acid, heating the reaction product in the presence of a reducing agent, and reacting the reaction mixture with an acyl halide represented by the general formula (III)

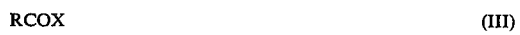

RCOX (III)

wherein R has the same meaning as defined above and X represents a halogen atom is disclosed.

24 Claims, No Drawings

METHOD FOR PREPARING 8-ACYLTHIO-1,2,3,4,5,6-HEXAHYDRO-2,6-METHANO-3,6(E),11(A)-TRIMETHYL-3-BENZAZOCINES

BACKGROUND OF THE INVENTION

The present invention relates to a method for preparing 3-benzazocine derivatives, more particularly, to a method for preparing 8-acylthio-1,2,3,4,5,6-hexahydro-2,6-methano-3,6(e),11(a)-trimethyl-3-benzazocines represented by general formula (I)

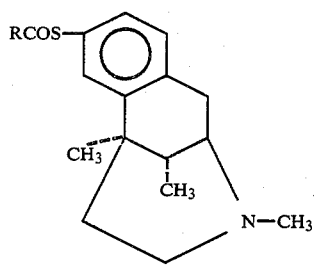

(I)

wherein R represents an alkyl group, a phenyl group or a heterocyclic group from 1,2,3,4,5,6-hexahydro-2,6-methano-3,6(e),11(a)-trimethyl-3-benzazocine represented by the formula (II)

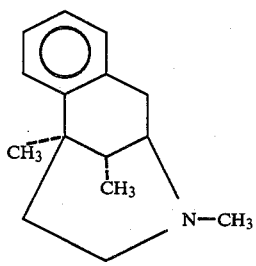

(II)

It is known that the type of compounds represented by general formula (I) are analgesic compounds which are non-addictional and can show pharmacological effects by oral administration as described in Japanese patent applications (OPI) Nos. 124281/1978, 61181/1979 and 13253/1980.

In the above published applications there are described the following synthetic pathways.

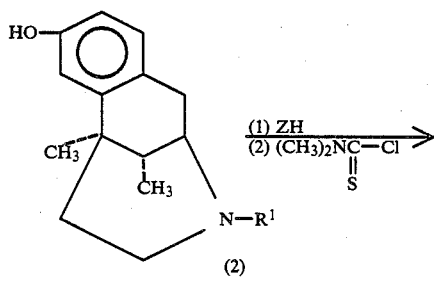

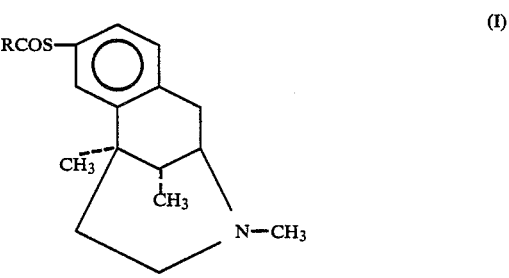

However, these methods for preparing benzazocine derivatives are disadvantageous in that narcotic compounds represented by the formula (2) must be used as a starting material and the methods comprise many steps.

SUMMARY OF THE INVENTION

With view to obviating the above disadvantages, extensive researches have been made and as a result thereof it has now been found that it is possible to avoid use of narcotic compounds as a starting compound and simplify synthetic steps by selecting the compound represented by the formula (II) as a starting compound.

The present invention is based on the above finding and provides a method for preparing 8-acylthio-1,2,3,4,5,6-hexahydro-2,6-methano-3,6(3),11(a)-trimethyl-3benzazocines represented by general formula (I)

(I)

wherein R represents an alkyl group, a phenyl group or a hetero cyclic group which comprises reacting 1,2,3,4,5,6-hexahydro-2,6-methano-3,6(e),11(a)-trimethyl-3-benzazocine represented by the formula (II)

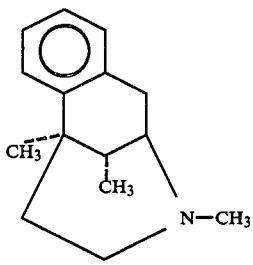

(II)

or its salt with chlorosulfonic acid, heating the reaction product in the presence of a reducing agent, and reacting the reaction mixture with an acyl halide represented by general formula (III)

RCOX  (III)

wherein R has the same meaning as defined above; and X represents a halogen atom.

DETAILED DESCRIPTION OF THE INVENTION

In the formula (I), the alkyl group represented by R has 1 to 10 carbon atoms, preferably 1 to 6 carbon atoms, such as a methyl group, an ethyl group, a propyl group, a butyl group, a hexyl group, etc.

The phenyl group represented by R may be unsubstituted or substituted with a halogen atom such as chlorine, etc., an alkyl group having 1 to 6 carbon atoms, preferably 1 to 4 carbon atoms, such as a methyl group, an ethyl group, etc., an alkoxy group having 1 to 6 carbon atoms, preferably 1 to 4 carbon atoms, such as a methoxy group, etc. and the like. Examples of the phenyl group represented by R include a phenyl group, a chlorophenyl group, a tolyl group, an ethylphenyl group, a methoxyphenyl group, etc.

The heterocyclic group represented by R is a 5- or 6-membered heterocyclic group containing as hetero atom a nitrogen atom or a nitrogen and one element selected from the group consisting of a nitrogen atom, a sulfur atom and an oxygen atom.

Examples of the heterocyclic group represented by R include a pyrrolyl group, a furyl group, a thiazolyl group, a pyranyl group, a pyridyl group, a pyrimidyl group, a morpholino group, etc.

Practically, there is no need to select complicated or expensive groups for R.

Further, it is sufficient to select chlorine or bromine as the halogen atom in the acyl halide represented by general formula RCOX.

Chlorosulfonic acid can be used in an amount of 1 to 3 mols, preferably 1.5 to 2.5 mols, per mol of the compound of the formula (II).

As the reducing agent, complex metal hydrides, a combination of a metal and an acid, etc. can be used in the present invention, with complex metal hydrides being preferred since they can be handled with ease. For example, lithium aluminum hydride and a reducing agent having the same or higher reducing power such as magnesium aluminum hydride, aluminum borohydride, etc. are preferred. Further, in order to obtain a sufficient reducing power, magnesium chloride, anhydrous aluminum chloride or a like additive can be added to sodium borohydride or calcium borohydride.

Examples of the metal-acid system include a combination of Zn—$H_2SO_4$ and of Sn—HCl. Further, sodium dihydro-bis (2-methoxyethoxy) aluminate can also be used as a reducing agent.

Heating can be carried out at a temperature not higher than the boiling point of solvents used. Preferably, heating is carried out under reflux.

These reducing agents can be used as a solution or suspension in an inert solvent which does not react with the substrate and reagent, such as ether, tetrahydrofuran, etc. as carried out conventionally.

The reducing agent can be used in an amount of 1 to 10 mols, perferably 3 to 8 mols, per mol of the compound of the formula (II).

It is preferred that unused chlorosulfonic acid be removed by evaporation after it is reacted with the compound represented by the formula (II) or its salt.

It is also preferred that the reducing be carried out in an appropriate solvent such as ether, tetrahydrofuran, dioxane, dioxolane, benzene, toluene, water, etc., under reflux. The solvent is selected depending on the reducing agent.

The acyl halide represented by general formula (III) can be used in an amount of 1 to 15 mols, preferably 5 to 10 mols, per mol of the compound of the formula (II).

Further, the method of the present invention can be carried out in one pot reaction without isolating intermediates formed in the respective steps.

For example, as will be clear from confirmation test for intermediate described hereinafter, an intermediate represented by general formula (III)

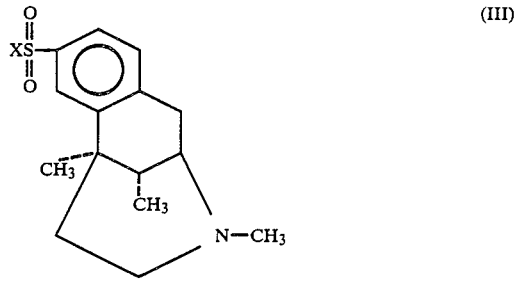

(III)

wherein X represents a halogen atom is formed in the prior step of the method of the present invention but this intermediate need not be isolated for further steps, and the method can be carried out substantially in one step.

The starting material, i.e., compound of formula (II) can be prepared with ease as illustrated below

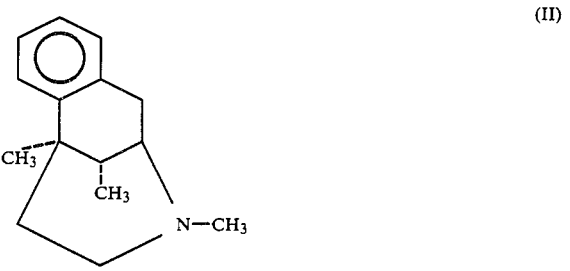

(II)

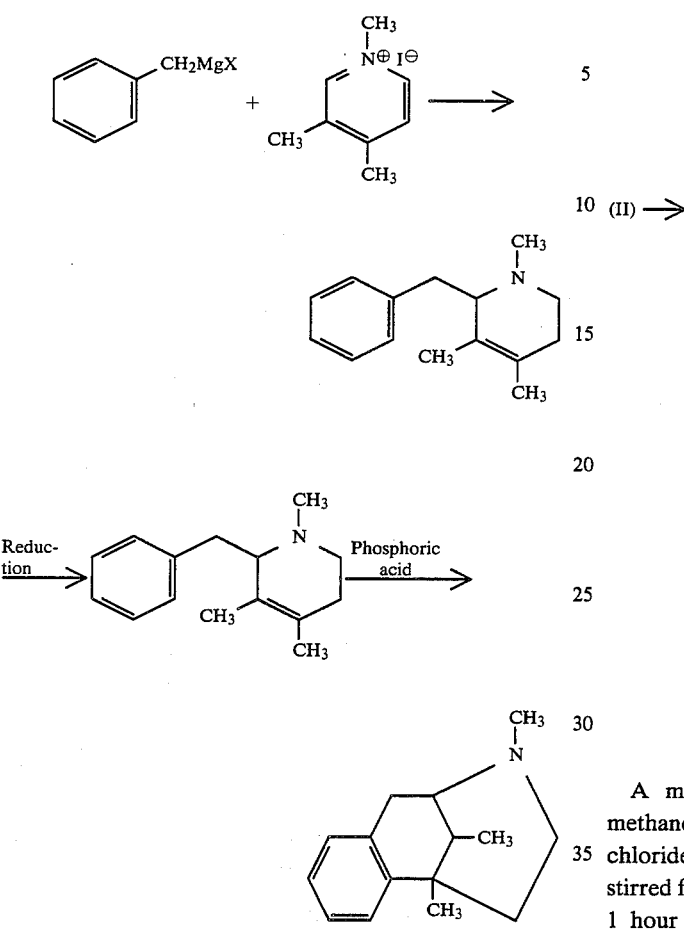

as described in *Jr. Org. Chem.*, 22, 1366-69 (1957).

According to the method of the present invention compounds of general formula (II) can be prepared from a compound of formula (I) in a yield of about 70% or even higher in contrast to the above-described conventional method which gives rise to the objective compound in a yield of 50% or so using the compound of the formula (2) as a starting compound.

It should be noted that the method of the present invention is very advantageous for use in practice on an industrial scale since not only the objective compounds of general formula (II) are non-narcotic but also the starting materials and intermediate compounds are non-narcotic and since the intermediate compounds need not be isolated during the course of reactions in contrast to conventional methods, and thus the method of the present invention can be carried out without limitation or restrains.

Hereinafter, the present invention will be described in greater detail with reference to the following examples which should be construed as being non-limitative.

REFERENCE EXAMPLE

Confirmation Test for Intermediate

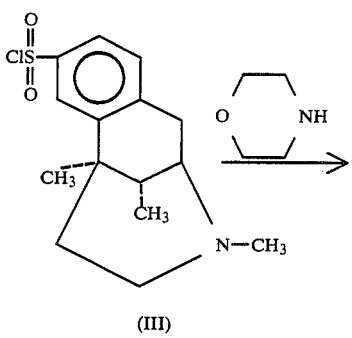

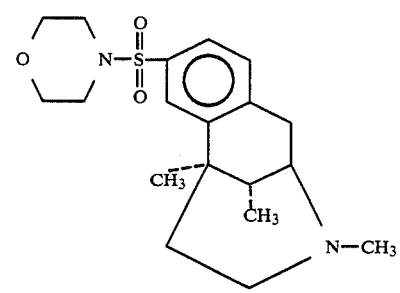

A mixture of 1.0 g of 1,2,3,4,5,6-hexahydro-2,6-methano-3,6(e),11(a)-trimethyl-3-benzazocine hydrochloride and 1 ml of chlorosulfonic acid ($ClSO_3H$) was stirred for 1 hour under ice cooling and then for another 1 hour at room temperature. After removing excess $ClSO_3H$ by evaporation under reduced pressure, 3 ml of morpholine was added to the reaction mixture. The resulting mixture was heated on an water bath to dissolve solid matters. The solution was poured into an aqueous solution of 10% $K_2CO_3$, extracted with ether, dried over $K_2CO_3$ followed by evaporation of the solvent to obtain 0.37 g of crude crystals. Recrystallization from ether gave rise to colorless prisms having a melting point of 145°–146° C.

(a) Elemental Analysis ($C_{19}H_{28}N_2O_3S$)

|  | C | H | N |
|---|---|---|---|
| Calculated: | 62.61 | 7.74 | 7.69 |
| Found: | 62.40 | 7.67 | 7.68 |

(b) IR$\nu_{max}^{KBr}$cm$^{-1}$: 1345, 1160

(c) Mass Spectrum m/e: 364 ($M^5$)

(d) NMR ($CDCl_3$) δ: 0.84 (3H, d, $CH_3$); 1.42 (3H, s, $CH_3$); 2.40 (3H, s, N—$CH_3$); 2.76-3.10, 3.60-3.90 (4H, 4H, m morpholine H); 7.15-7.68 (3H, m, Ar—H).

EXAMPLE 1

Preparation of Compound of General Formula (I) in which R is phenyl

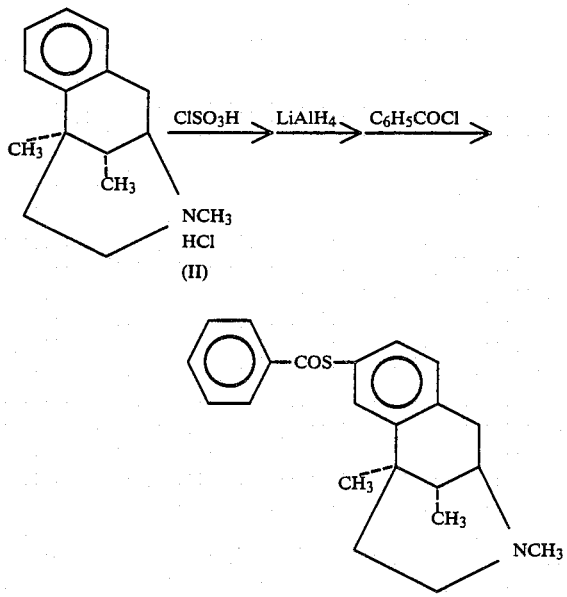

Chlorosulfonic acid (2 ml) was portionwise added to 2.0 g of 1,2,3,4,5,6-hexahydro-2,6-methano-3,6(e),11(a)-trimethyl-3-benzazocine hydrochloride with ice cooling, and the resulting mixture was stirred at 0° C. for 1 hour and at room temperature for 4 hours. After evaporating off excessive chlorosulfonic acid under reduced pressure, the reaction product contained in 25 ml of tetrahydrofuran solution was added dropwise to 25 ml of ether solution having dissolved therein 1.2 g of $LiAlH_4$. The resulting mixture was heated under reflux for 4 hours. Under ice cooling, a solution prepared from 10 ml of benzoyl chloride and 50 ml of ether was portionwise added to the reaction mixture, and the resulting mixture was stirred at room temperature for 1 hour. Then, the mixture was neutralized with an aqueous solution of 10% sodium hydroxide, extracted with ether, dried over $K_2CO_3$ followed by evaporation of the solvent. The residue was purified through silica gel chromatography ($C_6H_6$-ether: triethylamine=10:1) to obtain 1.64 g (yield: 80%) of 8-benzoylthio-1,2,3,4,5,6-hexahydro-2,6-methano-3,6(e),11(a)-trimethyl-3-benzazocine as an oily product.

(a) NMR (CDCl$_3$) δ:0.86 (3H, d,J=7 HZ, $C_{11}$—CH$_3$); 1.40 (3H, s, $C_6$—CH$_3$); 2.44 (3H, s, N—CH$_3$); 7.00–7.65 (6H, m, Ar—H); 7.90–3.15 (2H, m, Ar—H)

(b) IR$\nu_{max}^{neat}$cm$^{-1}$: 1675 (C=O)

(c) Fumarate of the above-described product:
Melting Point: 153°–154° C., colorless needles (recrystallized from acetone)
Elemental Analysis (C$_{22}$H$_{25}$NOS.C$_4$H$_4$O$_4$.H$_2$O)

| | C | H | N |
| --- | --- | --- | --- |
| Calculated: | 64.30 | 6.43 | 2.88 |
| Found: | 64.28 | 6.19 | 2.71 |

(d) Chloride of the above-described product:
Melting Point: 220°–222° C. (decomp.), colorless needles (recrystallized from acetone)
Elemental Analysis (C$_{22}$H$_{25}$NOS.HCl.½H$_2$O)

| | C | H | N |
| --- | --- | --- | --- |
| Calculated: | 66.56 | 6.85 | 3.52 |
| Found: | 66.48 | 6.75 | 3.42 |

EXAMPLE 2

Preparation of Compound of General Formula (I) in which R is 3-Pyridyl

Chlorosulfonic acid (20 ml) was added portionwise to 10 g of compound of formula (I) with ice cooling, and the mixture was stirred at room temperature. After 4 hours, 20 ml of ether was added to the reaction mixture and the ether was evaporated off together with remaining chlorosulfonic acid. Tetrahydrofuran (200 ml) was added to the residue to which 15 g of aluminum lithium hydride was added. The resulting mixture was heated under reflux. Then, a solution of 105 g of nicotinoyl chloride in 200 ml of ether was added to the mixture dropwise, and the resulting mixture was stirred for 12 hours. Then, the reaction mixture was rendered alkaline with the addition of an aqueous solution of 10% potassium carbonate, and extracted with ether. After the ether extract was dried over potassium carbonate, the ether solution was purified through silica gel column chromatography (developing solvent is ethyl acetate : hexane : triethylamine=1:1:0.2) to obtain 8.0 g of 1,2,3,4,5,6-hexahydro-2,6-methano-3,6(e),11(a)-trimethyl-8-nicotinoylthio-3-benzazocine in a yield of 77.5%. The compound has the following properties and appears as an colorless oily product.

(a) IR$\nu_{max}^{neat}$cm$^{-1}$: 1675 (C=O)

(b) NMR (CDCl$_3$) δ: 0.86 (3H, d, =CHCH$_3$); 1.40 (3H, s, C—CH$_3$); 2.42 (3H, s, —N—CH$_3$); 6.90–7.53 (4H, m, arom. H); 8.28, 8.80, 9.23 (each 1H, m, pyridine ring proton)

(c) Fumarate:
Melting point: 153° C.
Elemental Analysis (C$_{21}$H$_{24}$N$_2$OS.C$_4$H$_4$O$_4$)

| | C | H | N |
| --- | --- | --- | --- |
| Calculated: | 64.08 | 6.02 | 5.98 |
| Found: | 63.83 | 6.11 | 5.93 |

The same objective compound was obtained when the hydrochloride of compound of formula (I) was employed instead of free compound of formula (I).

EXAMPLE 3

Preparation of Compound of General Formula (I) in which R is p-Chlorophenyl

The same procedures as in Example 1 were repeated using 10 g of compound of formula (I), 20 Ml of chlorosulfonic acid, 15 g of aluminum lithium hydride and 100 g of p-chlorobenzoyl chloride to isolate 13.1 g or colorless oily product of 8-(p-chlorobenzoylthio)-1,2,3,4,5,6-hexahydro-2,6-methano-3,6(e),11(a)-trimethyl-3-benzazocine.

Yield: 72.5%

(a) IR$\nu_{max}^{neat}$cm$^{-1}$: 1675 (C=O)

(b) NMR (CDCl$_3$) δ: 0.87 (3H, d, CH—CH$_3$); 1.39 (3H, s, C—CH$_3$); 2.42 (3H, s, =N—CH$_3$); 7.18–7.60 (5H, m, arom. H); 7.89–8.12 (2H, m, arom, H)

(c) Fumarate:
Melting Point: 165°6° C. (decomp.)

Elemental Analysis ($C_{22}H_{24}NOSCl \cdot C_4H_4O_4$)

|  | C | H | N |
|---|---|---|---|
| Calculated: | 62.20 | 5.62 | 2.79 |
| Found: | 62.45 | 5.78 | 3.08 |

The same objective compound was obtained when sulfate of compound of formula (I) was employed.

EXAMPLE 4

Preparation of Compound of General Formula (II) in which R is p-Methoxyphenyl

The same procedures as in Example 1 were repeated using 10 g of compound of formula (I), 20 ml of chlorosulfonic acid, 15 g of aluminum lithium hydride and 100 g of p-methoxybenzoyl chloride to isolate 12.8 g (yield: 72%) of 1,2,3,4,5,6-hexahydro-2,6-methano-8-(p-methoxybenzoylthio)-3,6(e),11(a)-trimethyl-3-benzazocine. The compound appeared as colorless oily product.

(a) IR$\nu_{max}^{neat}$cm$^{-1}$: 1660 (C=O)
(b) NMR (CDCl$_3$) δ: 0.86 (3H, d, CH—CH$_3$); 1.40 (3H, s, C—CH$_3$); 2.45 (3H, s, N—CH$_3$); 3.88 (3H, s, OCH$_3$); 7.10–7.40 (3H, m, arom. H); 7.46 (4H, m, arom. H)
(c) Fumarate:
Melting Point: 201°–2° C.
Elemental Analysis ($C_{23}H_{27}NO_2S \cdot C_4H_4O_4$)

|  | C | H | N |
|---|---|---|---|
| Calculated: | 65.17 | 6.28 | 2.81 |
| Found: | 65.40 | 6.26 | 2.61 |

EXAMPLE 5

Preparation of Compound of General Formula (II) in which R is Methyl

The same procedures as in Example 1 were repeated using 10 g of compound of formula (I), 20 ml of chlorosulfonic acid, 15 g or sodium borohydride and 2 g of anhydrous aluminum chloride and 60 g of acetyl bromide to isolate 9.4 g (yield 70% of 8-acetylthio-1,2,3,4,5,6-hexahydro-2,6-methano-3,6(e),11(a)-trimethyl-3-benzazocine as a colorless oily product.

(a) IR$\nu_{max}^{neat}$cm$^{-1}$: 1710 (C=O)
(b) NMR (CDCl$_3$) δ: 0.84 (3H, d, CH—CH$_3$); 137 (3H, s, C—CH$_3$); 2.41 (6H, s, COCH$_3$, N—CH$_3$); 7.10–7.30 (3H, m, arom. H)
(c) Boiling Point: 130°–5° C. (0.5 mmHg)
(d) Elemental Analysis ($C_{17}H_{23}NOS$)

|  | C | H | N |
|---|---|---|---|
| Calculated: | 70.55 | 8.01 | 4.84 |
| Found: | 70.26 | 8.10 | 4.86 |

The same objective compound was obtained when acetate of compound of formula (I) was employed.

EXAMPLE 6

Preparation of Compound of General Formula (II) in which R is T-Butyl

The same procedures as in Example 1 were repeated using 10 g of compound of formula (I), 20 ml of chlorosulfonic acid, 15 g of aluminum lithium hydride, 89 g or pivaloyl chloride to isolate 10.5 g (yield: 67%) of 1,2,3,4,5,6-hexahydro-2,6-methano-3,6(e),11(a)-trimethyl-8-pivaloylthio-3-benzazocine as a colorless oily product.

(a) IR$\nu_{max}^{neat}$cm$^{-1}$: 1695 (C=O)
(b) NMR (CDCl$_3$) δ: 0.86 (3H, d, CH—CH$_3$); 1.33 (9H, s, C(CH$_3$)$_3$); 1.38 (3H, s, C—CH$_3$); 2.42 (3H, s, N—CH$_3$); 7.08–7.28 (3H, m, arom. H)
(c) Fumarate:
Melting Point: 182°–5° C.
Elemental Analysis ($C_{20}H_{29}NOS \cdot C_4H_4O_4$)

|  | C | H | N |
|---|---|---|---|
| Calculated: | 64.40 | 7.43 | 3.13 |
| Found: | 63.98 | 7.50 | 3.01 |

EXAMPLE 7

Preparation of Compound of General Formula (I) in which R is Phenyl

Chlorosulfonic acid (20 ml) was added portionwise to 10 g of compound of formula (II) under ice cooling, and the mixture was stirred at room temperature. After 4 hours, 20 ml of ether was added to the reaction mixture and the ether was evaporated off together with remaining chlorosulfonic acid. Benzene (200 ml) was added to the residue to which a solution of 10.1 g of sodium dihydrobis (2-methoxyethoxy) aluminate in 40 ml of benzene was added portionwise. The resulting mixture was heated under reflux for 2 hours. Then, a solution of 90 g of benzoyl chloride in 200 ml of benzene was added to the mixture dropwise, and the resulting mixture was stirred for 12 hours. Then, the reaction mixture was decomposed with the addition of 25% sulfuric acid, and benzene layer was separated. Aqueous layer was extracted twice each with 50 ml of benzene, and dried over potassium carbonate. After benzene was removed by evaporation the residue was dissolved in ether and the ether solution was purified through silica gel column chromatography (developing solvent was ethyl acetate: hexane: triethylamine=1:1:0.2) to obtain 7.8 g of 8-benzoylthio-1,2,3,4,5,6-hexahydro-2,6-methano-3,6(e),11(a)-trimethyl-8-nicotinoylthio-3-benzazocine as colorless oily product in a yield of 70%. The compound has the following properties.

(a) IR$\nu_{max}^{neat}$cm$^{-1}$: 1675 (C=O)
(b) NMR (CDCl$_3$) δ: 0.87 (3H, d, CH—CH$_3$); 1.39 (3H, s, C—CH$_3$); 2.42 (3H, s, =N—CH$_3$); 7.18–7.60 (5H, m, arom. H); 7.89–8.12 (2H, m. arom. H)
(c) Fumarate:
Melting Point: 153°–4° C.
Elemental Analysis ($C_{22}H_{25}NOS \cdot C_4H_4O_4$)

|  | C | H | N |
|---|---|---|---|
| Calculated: | 64.79 | 6.25 | 3.00 |
| Found: | 66.69 | 6.22 | 3.08 |

EXAMPLE 8

Preparation of Compound of General Formula (II) in which R is Phenyl.

Chlorosulfonic acid (5 ml) was added portionwise to 5.16 g of compound of formula (II) under ice cooling, and the mixture was heated on a boiling water bath for 30 minutes. Then, a mixture of 20 g of sulfuric acid and 60 g of water was added portionwise to the reaction mixture. After the addition of 10 g of zinc powder the mixture was heated on a boiling water bath for 6 hours. After cooling 30 ml of benzoyl chloride was added to the reaction mixture, to which was portionwise added with stirring 120 ml of an aqueous 30% potassium carbonate and then 150 ml of benzene. The resulting mixture was stirred at room temperature 12 hours. After benzene layer was separated, aqueous layer was extracted twice each with 10 ml of benzene. The extract was dried over $K_2CO_3$ and benzene was removed by evaporation. The residue was dissolved in ether and the ether solution was purified through silica gel column chromatography (developing solution was ethyl acetate: hexane: triethylamine=1:1:0.2) to obtain 13.68 g (yield: 43%) of 8-benzoylthio-1,2,3,4,5,6-hexahydro-2,6-methano-3,6(e),11(a)-trimethyl-3-benzazocine as colorless oily product. The compound had the following properties.

(a) $IR\nu_{max}^{neat}cm^{-1}$: 1675 (C=O)

(b) NMR ($CDCl_3$) δ: 0.87 (3H, d, CH—$CH_3$); 1.39 (3H, s, C—$CH_3$); 2.42 (3H, s, =N—$CH_3$); 7.18–7.60 (5H, m, arom. H); 7.89–8.12 (2H, m, arom. H)

(c) Fumarate:
Melting point: 153°–4° C.
Elemental Analysis ($C_{22}H_{25}NOS \cdot C_4H_4O_4$)

|  | C | H | N |
| --- | --- | --- | --- |
| Calculated: | 66.79 | 6.25 | 3.00 |
| Found: | 66.79 | 6.33 | 3.10 |

While the invention has been described in detail and with reference to specific embodiment thereof, it will be apparent to one skilled in the art that various changes and modifications can be made therein without departing from the spirit and scope thereof.

What is claimed is:

1. A method for preparing 8-acylthio-1,2,3,4,5,6-hexahydro-2,6-methano-3,6(e),11(a)-trimethyl-3-benzazocines represented by formula (I) below:

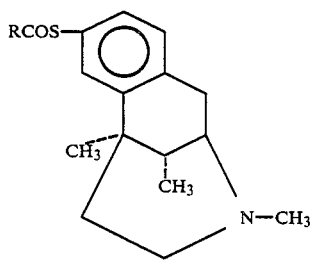

(I)

wherein R represents an alkyl group having 1 to 10 carbon atoms, a phenyl group or a 5- or 6-membered heterocyclic group wherein the hetero atom is a nitrogen atom or a nitrogen atom and one element selected from the group consisting of a nitrogen atom, a sulfur atom and an oxygen atom, which comprises reacting 1,2,3,4,5,6-hexahydro-2,6-methano-3,6(e),11(a)-trimethyl-3-benzazocine represented by formula (II) below:

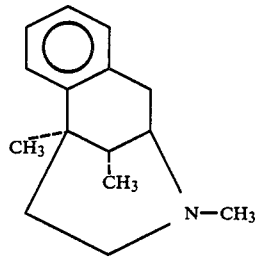

(II)

or its salt with chlorosulfonic acid, heating the reaction product in the presence of a reducing agent, and reacting the reaction mixture with an acyl halide represented by formula (III)

RCOX (III)

wherein R has the same meaning as defined above and X represents a halogen atom.

2. The method as claimed in claim 1, wherein said alkyl group represented by R has 1 to 6 carbon atoms.

3. The method as claimed in claim 1, wherein said phenyl group represented by R is substituted with a halogen atom, an alkyl group having 1 to 6 carbon atoms or an alkoxy group having 1 to 6 carbon atoms.

4. The method as claimed in claim 3, wherein said alkyl group has 1 to 4 carbon atoms.

5. The method as claimed in claim 3, wherein said alkoxy group has 1 to 4 carbon atoms.

6. The method as claimed in claim 3, wherein said phenyl group represented by R is selected from the group consisting of a phenyl group, a chlorophenyl group, a tolyl group, an ethylphenyl group and a methoxyphenyl group.

7. The method as claimed in claim 1, wherein said heterocyclic group represented by R is selected from the group consisting of a pyrrolyl group, a furyl group, a thiazolyl group, a pyranyl group, a pyridyl group, a pyrimidyl group and a morpholino group.

8. The method as claimed in claim 1, wherein said halogen atom represented by X is chlorine or bromine.

9. The method as claimed in claim 1, wherein said chlorosulfonic acid is used in an amount of 1 to 3 mols per mol of the compound of formula (II).

10. The method as claimed in claim 9, wherein said chlorosulfonic acid is used in an amount of 1.5 to 2.5 mols per mol of the compound of formula (II).

11. The method as claimed in claim 1, wherein said heating is carried out in a solvent.

12. The method as claimed in claim 11, wherein said heating is carried out under reflux.

13. The method as claimed in claim 1, wherein said reducing agent is a complex metal hydride or a combination of a metal and an acid.

14. The method as claimed in claim 13, wherein said reducing agent is a complex metal hydride.

15. The method as claimed in claim 14, wherein said complex metal hydride is aluminum lithium hydride or aluminum magnesium hydride.

16. The method as claimed in claim 13, wherein said combination of a metal and an acid is a combination of zinc and sulfuric acid or a combination of tin and hydrochloric acid.

17. The method as claimed in claim 16, wherein said combination of a metal and an acid is a combination of zinc and sulfuric acid.

18. The method as claimed in claim 1, wherein said reducing agent is sodium dihydro-bis (2-methoxyethoxy)-aluminate.

19. The method as claimed in claim 1, wherein said reducing agent further comprises an additive for strengthening the reducing power of said complex metal hydride.

20. The method as claimed in claim 19, wherein said additive is anhydrous aluminum chloride or magnesium chloride.

21. The method as claimed in claim 1, wherein said reducing agent is used in an amount of 1 to 10 mols per mol of the compound of formula (II).

22. The method as claimed in claim 21, wherein said reducing agent is used in an amount of 3 to 8 mols per mol of the compound of formula (II).

23. The method as claimed in claim 1, wherein said acyl halide is used in an amount of 1 to 15 mols per mol of the compound of formula (II).

24. The method as claimed in claim 1, wherein said acyl halide is used in an amount of 5 to 10 mols per mol of the compound of formula (II).

* * * * *